United States Patent [19]

Katsumata et al.

[11] Patent Number: 4,541,964
[45] Date of Patent: Sep. 17, 1985

[54] PRODUCTION OF METHACRYLONITRILE

[75] Inventors: Tsutomu Katsumata, Yokohama; Tetsuro Dozono, Yokosuka, both of Japan

[73] Assignee: Asahi Kasei Kasyo Kabushiki Kaisha, Osaka, Japan

[21] Appl. No.: 644,152

[22] Filed: Aug. 27, 1984

Related U.S. Application Data

[63] Continuation of Ser. No. 421,072, Sep. 22, 1982, abandoned.

[30] Foreign Application Priority Data

Oct. 26, 1981 [JP] Japan ................... 56-170106

[51] Int. Cl.$^4$ .................. C07C 120/14; C07C 120/00
[52] U.S. Cl. ........................ 260/465.3; 260/465.9; 502/212; 502/243
[58] Field of Search ................ 260/465.3, 465.9

[56] References Cited

U.S. PATENT DOCUMENTS

| | | | |
|---|---|---|---|
| 3,712,912 | 1/1973 | Hausweiler et al. | 260/465.3 |
| 3,766,092 | 10/1973 | Honda et al. | 252/437 |
| 4,000,176 | 12/1976 | Umemura et al. | 260/465.3 |
| 4,001,317 | 1/1977 | Grasselli et al. | 260/533 N |
| 4,009,194 | 2/1977 | Umemura et al. | 260/465.3 |
| 4,036,870 | 7/1977 | Castellion | 260/465.3 |
| 4,070,390 | 1/1978 | Umemura et al. | 260/465.3 |
| 4,123,453 | 10/1978 | Grasselli et al. | 260/465.3 |
| 4,139,552 | 2/1979 | Grasselli et al. | 260/465.3 |
| 4,182,907 | 1/1980 | Grasselli et al. | 562/546 |
| 4,192,776 | 3/1980 | Grasselli et al. | 252/432 |
| 4,228,098 | 10/1980 | Aoki et al. | 260/465.3 |
| 4,290,922 | 9/1981 | Umemura et al. | 252/456 |
| 4,323,520 | 4/1982 | Hardman et al. | 260/465.9 |

FOREIGN PATENT DOCUMENTS

| | | |
|---|---|---|
| 16419 | 1/1972 | Japan . |
| 17334 | 2/1980 | Japan . |
| 17356 | 2/1980 | Japan . |
| 22639 | 2/1980 | Japan . |
| 1319190 | 6/1973 | United Kingdom . |
| 1347175 | 2/1974 | United Kingdom . |

OTHER PUBLICATIONS

Brunauer et al., "Adsorption of Gases on Multimolecular Layers", J. Am. Chem. Soc., 60, 309-319 (1938).

Primary Examiner—Joseph Paul Brust
Attorney, Agent, or Firm—Pennie & Edmonds

[57] ABSTRACT

In the preparation of methacrylonitrile by gas-phase ammoxidation of isobutylene or tertiary butanol, the reaction is carried out (A) (i) using a catalyst system consisting essentially of (1) 30-70% by weight of a silica catalyst carrier and (2) a catalyst material having a composition represented by the formula:

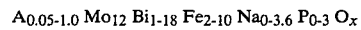

$$A_{0.05-1.0} Mo_{12} Bi_{1-18} Fe_{2-10} Na_{0-3.6} P_{0-3} O_x$$

wherein A is at least one element selected from the group consisting of potassium, rubidium and cesium, and x is the number of oxygen atoms needed to satisfy the valence requirements of the other elements present, said catalyst system having a specific surface area of 2-10 m$^2$/g; (ii) at a temperature of 380°-480° C.; (iii) at a contact time of 1-10 seconds; and (B) while maintaining the oxygen concentration in the gaseous reaction mixture below about 1 percent by volume.

7 Claims, No Drawings

PRODUCTION OF METHACRYLONITRILE

This is a continuation of application Ser. No. 421,072, filed Sept. 22, 1982, now abandoned.

TECHNICAL FIELD

The present invention relates to the production of methacrylonitrile by ammoxidation, i.e., by contacting tert-butanol or isobutylene, in the gaseous phase at elevated temperature, with ammonia and oxygen in the presence of a silica-supported multiple oxide promoter or catalyst containing molybdenum, bismuth and iron.

BACKGROUND ART

It is known that methacrylonitrile can be produced by catalytic ammoxidation of isobutylene in the gas phase at elevated temperature, and a number of catalysts have been proposed for this purpose. For example, Japanese laid-open patent application No. 49719/1973 discloses a multiple metal oxide catalyst system whose basic components are molybdenum, bismuth, iron, and cobalt or nickel. However, although subsequent improvements have been made on various aspects of catalyst systems of this type, when they are employed for the ammoxidation of isobutylene or tert-butanol, the yield of desired methacrylonitrile drops markedly within a short period of time. This adversely affects the suitability of such catalysts for industrial use.

In Japanese laid-open patent application Nos. 17334/1980 and 17356/1980, the present inventors disclosed an improved method for producing methacrylonitrile by gas-phase ammoxidation of tert-butanol or isobutylene at elevated temperature by means of a catalyst containing molybdenum, bismuth and iron as basic components, and further containing a trace amount of at least one element selected from potassium, rubidium and cesium. However, while improvements have thus been made in product yield as well as in catalyst life and stability, the formation of carbon deposits on the catalyst has continued to be a problem, particularly since methacrylonitrile readily undergoes oxidative decomposition whereby such deposits are formed. This results in increased co-production of methacrolein which makes it more difficult to isolate and purify the desired methacrylonitrile and adversely affects the yield of the latter. Although it is possible to regenerate the catalyst by burning off the carbon deposits, this requires interruption of the ammoxidation reaction which is a serious economic drawback, particularly in cases where the process is intended for continuous operation, e.g., in a fluidized bed-type reactor.

Thus, there has been a long-felt need for and extensive studies have been made to develop an improved industrial catalyst and process for the commercial production of methacrylonitrile by ammoxidation of tert-butanol or isobutylene. In particular, an ammoxidation catalyst and process has long been sought which is suitable for use in a fluidized bed reactor, has high catalytic activity and high product selectivity, and has a long use life unhampered by the formation of carbon deposits on the surface of the catalyst.

DISCLOSURE OF THE INVENTION

The foregoing objects are achieved according to the present invention by means of a catalyst composition containing certain proportions of molybdenum, bismuth and iron and at least one element selected from potassium, rubidium and cesium, and having a surface area of 2-10 m$^2$/g. Through this discovery, it has been found that the formation of carbon deposits on the catalyst can be suppressed and also product selectivity greatly improved; that the fugacity of the molybdenum (i.e., the tendency of the molybdenum to escape from the catalyst by sublimation) can be suppressed with the use of sodium; that high abrasion resistance can be imparted to the catalyst by the use of silica as the catalyst carrier and by the addition of a small quantity of phosphorus; and that the activity and selectivity of the catalyst can greatly be improved by carrying out the reaction at a temperature of 380°–480° C., at atmospheric pressure or above, for a contact time of 1 to 10 seconds, and maintaining the oxygen concentration in the gas mixture at the outlet of the catalyst bed at 1 volume % or less.

More particularly, the present invention provides a process for producing methacrylonitrile by contacting tert-butanol or isobutylene with ammonia and oxygen in the gas phase in the presence of a solid catalyst system. The active component of the catalyst system is supported on silica and has a composition represented by the formula:

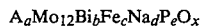

$$A_a Mo_{12} Bi_b Fe_c Na_d P_e O_x$$

wherein A is at least one element selected from the group consisting of potassium, rubidium and cesium; a, b, c, d, and e represent the numbers of atoms of A, bismuth, iron, sodium and phosphorus, respectively, relative to 12 atoms of molybdenum, i.e., a=0.05–1.0, b=1–18, c=2–10, d=0–3.6, and e=0–3; and x is the number of oxygen atoms needed to satisfy the valences of the other elements in the active catalyst component. The silica carrier constitutes between about 30 and about 70% by weight of the total catalyst system. The catalyst system has a surface area of between about 2 and about 10 m$^2$/g. The reaction is conducted at a temperature of about 380° to about 480° C. for a contact time of about 1 to about 10 seconds. The oxygen concentration in the gaseous reaction mixture at the outlet of the catalyst bed is maintained at or below about 1% by volume.

The catalyst used in the present invention is characterized in that it contains an essential component, A, described hereinabove and has a catalyst surface area of 2–10 m$^2$/g. In contrast, a catalyst containing no component A and/or having a surface area outside the range of the present invention is slower and/or less selective in producing methacrylonitrile. In such cases there would also be substantial and undesireable decomposition of the methacrylonitrile formed, with concomitant formation of carbon deposits on the catalyst. This is particularly true in commercial operations where it is desired to prolong the contact time of the tert-butanol or isobutylene with the catalyst so as to maximize the degree of conversion. But the rate of conversion of tert-butanol or isobutylene decreases and the amount of by-product methacrolein increases when carbon deposits occur on the catalyst. Accordingly, the yield of methacrylonitrile decreases while there is a remarkable increase in the formation of by-product methacrolein. The latter polymerizes readily during subsequent recovery and refining of methacrylonitrile. This tends to stain and clog distillation columns and drains. Alternatively, methacrolein can react with hydrogen cyanide present to form a cyanohydrin. For these reasons, co-production of methacrolein is highly undesirable in industrial methacrylonitrile manufacturing plants.

According to experiments conducted by the present inventors, the tert-butanol supplied to the reactor is converted to methacrylonitrile, methacrolein, carbon dioxide, carbon monoxide, acetonitrile, hydrogen cyanide and isobutylene; no tert-butanol starting material was detected at all in any of the reactions. In such circumstances, if one regards the detected isobutylene as a surrogate for the unreacted starting material, the term "conversion of tert-butanol" as used herein is defined as follows:

Total conversion of tert-butanol (%) =

$$\left(1 - \frac{\text{Carbon weight of remaining isobutylene}}{\text{Carbon weight of tert-butanol supplied}}\right) \times 100$$

When using the catalyst system of the present invention, high selectivity to methacrylonitrile can be achieved even at essentially 100% conversion of tert-butanol or isobutylene.

As indicated above, catalyst component, A, is selected from potassium, rubidium, and cesium, or a combination thereof; the quantity, a, of component, A, can vary from about 0.05 to 1.0. When A is potassium, the catalyst is more active than when A is cesium or rubidium. Accordingly, if potassium is used, the quantity, a, is preferably between about 0.1 and about 1.0. If A is cesium and/or rubidium, the quantity, a, is preferably between about 0.05 and about 0.6. In general, therefore, the quantity, a, is preferably between about 0.1 and about 0.6. If the level of component A exceeds the range of the present invention, the conversion rate of tert-butanol or isobutylene is reduced, with concomitant lower consumption of ammonia and an undesirable increase in by-product methacrolein.

As used herein, the term "surface area" refers to the area of the catalyst surface measured according to the method developed by Brunauer, Emmett and Teller (the "BET" method) and described by them in "Adsorption of Gases in Multimolecular Layers", J. Am. Chem. Soc., 60, 309–19 (1938). Such a surface area can be achieved by adjusting the calcination conditions to within a temperature range of about 650° to about 750° C. and within a time range of about 1 to about 10 hours or more. It has been found that a catalyst surface area less than about 2 m$^2$/g lowers the activity of the catalyst; this in turn lowers the conversion rate of tert-butanol or isobutylene and increases the amount methacrolein formed, both of which are undesirable. On the other hand, a catalyst surface area greater than about 10 m$^2$/g promotes the formation of unwanted carbon deposits on the catalyst and lowers the selectivity to methacrylonitrile formation.

Among the effective component ratios in the present catalyst, those of molybdenum, bismuth and iron can be selected so that bismuth ranges from about 1 to about 18 atoms and iron ranges from about 2 to about 10 atoms relative to 12 atoms of molybdenum, with ranges of about 2 to about 10 for bismuth and about 3 to about 10 for iron being preferred. When the ratio of bismuth to molybdenum and the ratio of iron to molybdenum are outside the limits of the present invention, the high selectivty to methacrylonitrile formation cannot be obtained even if component A is present and the catalyst surface area is within the aforesaid prescribed range.

The amount of optional sodium in the present catalyst can be selected within the range of 0 to about 3.6 atoms relative to 12 atoms of molybdenum. In this connection, it should be noted that when the proportion of molybdenum in the catalyst is high, the fugacity of that component is likewise relatively increased. However, this tendency of molybdenum to escape from the catalyst system can be suppressed effectively by addition of sodium in amounts within the range specified herein. When the molybdenum concentration in the catalyst is relatively small, its fugacity is inherently low enough to permit use of the catalyst in industrial applications without sodium.

In the catalyst system of the present invention, silica is used as the support or carrier. Silica per se is inert and relatively hard, compared with some other carriers; accordingly, it performs its function as a binder without materially impairing catalyst selectivity, and imparts a high degree of abrasion resistance to the catalyst system. When other carriers such as titania or zirconia are used, they have little effect as binders. On the other hand, alumina, which has the requisite binder effect, can greatly lower the selectivity of the catalyst. Even if the catalyst contains as little as 1% by weight aluminum, selectivity will be lowered noticeably. The amount of silica employed can range from 30–70% by weight of the total catalyst system, 40–60% by weight being especially preferred. At a level of at least 30% by weight of silica, good abrasion resistance is obtained. However, at a carrier level in excess of 70% by weight, the catalyst system is too dilute in active components and selectivity is greatly lowered.

The other optional component, phosphorus, can be used in an amount, e, ranging from 0 to about 3 atoms relative to 12 molybdenum atoms in the above formula. By adding a small quantity of phosphorus as aforesaid, the abrasion resistance of the catalyst system can further be improved. The added phosphorus comminutes and improves the dispersibility of the particles of suspended materials in preparing the starting slurry in the catalyst preparation step hereinafter described. Thus, the silica sol preferably used as the silica carrier source and the active catalyst components can be mixed together in a homogeneous state in the slurry to give excellent abrasion resistance in the final form of the catalyst. Although phosphorus can be used in excess of the range of the present invention, no further increase in abrasion resistance is attained thereby.

A catalyst to be used in an industrial process should retain its activity for a long time under the reaction conditions. The catalyst of the present invention not only has improved activity and selectivity at the initial stage of its use, it is also endowed with excellent stability and abrasion resistance. Thus, high catalytic activity and product selectivity are maintained for long periods of use.

The production of methacrylonitrile can be carried out according to the present invention in either a fluidized bed reactor or in a fixed bed reactor. Generally, the use of a fluidized bed facilitates removal of heat from the reaction to give a more uniform process temperature and for this reason is highly suitable for large scale production. And while catalysts normally employed in fluidized bed reactors are often abraded through collisions between catalyst particles or between the vessel wall and the particles, the catalyst of the present invention can withstand such abrasion.

The catalyst of the present invention is produced preferably by a three-step method comprising preparing a starting slurry, subsequently spray-drying said slurry and finally subjecting the dried material to a calcining heat treatment. Silica sol can be used as the silica carrier source, and phosphoric acid as the phosphorus source. Desirable sources of molybdenum, bismuth, iron, sodium, potassium, rubidium and cesium are the corresponding ammonium salts, nitrates, hydrochlorides, sulfates or organic acid salts soluble in water or nitric acid. In particular, the molybdenum source is preferably the ammonium salt of heptamolybdic acid; the preferred bismuth, iron, sodium, potassium, rubidium and cesium sources are their respective nitrates.

A starting slurry is prepared by first adding phosphoric acid to silica sol with stirring, followed by the addition of an aqueous ammonium molybdate solution, and finally a solution in dilute nitric acid of bismuth nitrate, ferric nitrate, sodium nitrate and at least one of potassium nitrate, rubidium nitrate and cesium nitrate. In this way one can obtain a slurry of minutely divided suspended materials dispersed uniformly in a silica colloid sol. The slurry is then spray-dried by conventional means to provide minute, spherically shaped, dried particles.

Spray-drying of the starting slurry can be performed by the centrifugal system, the bi-fluid nozzle system or the high pressure nozzle system conventionally used in industrial practice, the centrifugal system being preferred. Using the centrifugal system, a particle size distribution ranging from 10 to 150 microns, suitable for use in a fluidized bed reactor, is achieved by controlling the rotational speed of the disc and the rate at which the slurry is supplied. Finally, the dried product is subjected to a calcining heat treatment in a conventional tunnel or rotary-type kiln.

The calcination temperature and the calcination time are determined so as to control the catalyst surface area within the range of 2-10 $m^2/g$. The calcination temperature can vary within the range of about 650° to about 750° C., preferably 670°-730° C., and the calcination time, which is adjusted depending on the calcination temperature, can range from about 1 to about 20 hours. Since the catalyst surface area varies as a function of the catalyst composition even under the same calcination conditions, the latter should be selected carefully for each catalyst species employed.

In producing methacrylonitrile using the present catalyst, a most important process condition is the maintenance of an oxygen concentration of about 1 volume % or less in the gas mixture at the outlet of the catalyst bed, and preferably about 0.5 volume % or less.

In the ammoxidation of isobutylene or tert-butanol according to the prior art, carbon deposition on the catalyst was so marked as compared with ammoxidation of propylene that the concentration of oxygen in the gas mixture at the outlet of the catalyst bed had to be kept high, and it has been considered difficult to achieve stable running for long periods with 1 volume % or less oxygen in the outlet gas.

According to experiments by the present inventors, when ammoxidation of tert-butanol is carried out with 1 volume % or less of oxygen in the gas mixture at the outlet of the catalyst bed, using, for example the catalyst disclosed in Example 9 in Japanese laid-open patent application No. 16419/1972 or the catalyst disclosed in Example 15 in Japanese laid-open patent application No. 49719/1973, carbon deposits soon formed on the catalyst, and the reaction could not be continued.

In contrast, with the catalyst and process of the present invention, no deterioration of the catalyst on account of carbon deposition, reduction of catalyst use life, etc. was observed even at the low oxygen levels prescribed herein. On the contrary, according to the present invention, the conversion of tert-butanol or isobutylene is essentially 100% and selectivity to methacrylonitrile formation is good. On the other hand, when the oxygen level in the gas mixture at the catalyst bed outlet is 1 volume % or more, the conversion of tert-butanol or isobutylene is lowered, along with methacrylonitrile selectivity, a result which is contrary to common experience.

Thus, it is clear that if there is any deviation from the four essential elements of the present invention, namely, the trace component A; the proportions of molybdenum, bismuth and iron; the catalyst surface area; and the oxygen concentration in the gas mixture at the catalyst bed outlet, then methacrylonitrile cannot be produced in a satisfactory manner.

The tert-butanol or isobutylene starting material need not be of high purity. It is also possible to use a mixture of isobutylene and tert-butanol. Air can be used as the oxygen source.

The volume ratio of the total amount of tert-butanol and/or isobutylene to ammonia in the reaction generally ranges from 1:0.9–2.0, preferably 1:1–1.6.

The ratio of tert-butanol or isobutylene to oxygen in the reaction is a critical factor in the present invention inasmuch as it affects the oxygen concentration in the gas mixture at the outlet of the reactor. The oxygen concentration in the gas mixture at the reactor outlet is affected not only by the volume ratio of tert-butanol or isobutylene to oxygen, but also by the initial gas concentration, the reaction temperature, pressure, and the contact time between the catalyst and the gaseous reactants. Among these factors, the volume ratio of tert-butanol or isobutylene to oxygen exerts the strongest effect, and therefore should be determined with respect to the oxygen concentration in the gas mixture at the outlet of the reactor. As a general rule, the volume ratio of the total amount of tert-butanol and/or isobutylene to oxygen according to the present invention ranges between 1:1.8–2.6. It is also possible to introduce steam or an inert gas, if desired.

The reaction temperature can be 380°–480° C., and preferably 400°–460° C. When the reaction temperature is lower than about 380° C., the conversion of tert-butanol or isobutylene decreases abruptly. On the other hand, carbon deposits are likely to be formed, and increased amounts of molybdenum will tend to escape from the catalyst at reaction temperatures greater than about 480° C.

The reaction pressure can be normal or atmospheric pressure. The reaction can also be carried out at higher pressures, if desired.

The duration of contact between the gaseous reaction mixture and the catalyst can be 1 to 10 seconds, preferably 1.5 to 8 seconds. When the contact time is shorter than about 1 second, the conversion of tert-butanol or isobutylene decreases. On the other hand, with contact times longer about 10 seconds, substantial carbon deposition on the catalyst is likely to occur. The contact time greatly affects the oxygen concentration in the gas mixture at the outlet of the catalyst bed and therefore should be determined with a view toward maintaining the appropriate oxygen concentration.

As described above, the process of the present invention employs a specific catalyst and reaction conditions and has markedly improved selectivity to methacrylonitrile formation by ammoxidation of tert-butanol or isobutylene. It is also very advantageous for use on an industrial scale because of improvements which have been made with respect to the stability and abrasion resistance of the catalyst.

EXAMPLES

A further understanding of the present invention, and the advantages thereof, can be had by reference to the following examples.

(1) Preparation of catalysts

According to the procedure described below, an oxide catalyst was prepared having the formula $Mo_{12}Bi_{4.6}Fe_{4.9}K_{0.3}P_{1.0}$, carried at 50% by weight on silica. The numbers of oxygen atoms are omitted from the preceding catalyst formula and from the catalyst formulas in Tables 1 through 4 since the number of oxygen atoms needed to satisfy the valances of the other elements can be calculated from the given proportions of those elements. The valances of Mo, Bi, Fe, K (Na, Cs), and P are $+6$, $+3$, $+3$, $+1$, and $+5$, respectively.

Into 5000 g of a silica sol containing 30% by weight of $SiO_2$ ("Snowtex N" produced by Nissan Kagaku Co.) was added, with stirring, 52.8 g of 85% by weight of phosphoric acid, followed by a solution of 970 g of ammonium heptamolybdenate $[(NH_4)_6Mo_7O_{24}.4H_2O]$ dissolved in 2400 g of water, and finally a solution of 1020 g bismuth nitrate $[Bi(NO_3)_3.5H_2O]$, 906 g of ferric nitrate $[Fe(NO_3)_3.9H_2O]$, and 13.9 of potassium nitrate $[KNO_3]$ in 1000 g of nitric acid. The starting slurry thus obtained was transferred to a co-current type spray-drier. Spray-drying of the slurry was performed by means of a centrifugal spraying device equipped with a tray-type rotor arranged at the upper central portion of the drier. The resultant dried powders were subjected to precalcination in a tunnel type kiln at 300° C. for 2 hours, and then calcined at 690° C. for 4 hours.

The surface area of the catalyst was determined by the BET method, using a "Sorptograph Model ADS-1B" apparatus for measuring a quantity of absorbed gas and which is manufactured by Shimazu Seisakusho. The catalyst was placed in a sample tube and then accurately weighed (0.5074 g). A mixture of nitrogen gas and helium gas was introduced into the sample tube at a rate of 12.4 ml/minute of nitrogen and 24 ml/minute of helium. The sample tube was cooled in liquid nitrogen and the cooled catalyst adsorbed nitrogen from the gas mixture. After an equilibrium state of adsorption was reached, the sample tube was withdrawn from the liquid nitrogen and the sample tube was warmed to room temperature. The concentration of nitrogen in the gas mixture was increased by desorbing the nitrogen gas which had been adsorbed on the catalyst. The changes in nitrogen concentration due to adsorption and desorption were detected as peaks on a gas chromatograph which were recorded by a heat-transmission type detector, from which the area of the desorption peak was measured and found to be 1.511 $cm^2$. The quantity of nitrogen adsorbed on the catalyst was determined by multiplying this area by a factor obtained from the detecting peak and was found to be 0.495 ml (at 25.5° C.). The BET surface area was then calculated from the quantity of nitrogen adsorbed and the weight of the catalyst employed according to the BET theory and was found to be 3.0 $m^2$/g catalyst. (See catalyst No. 1 in Table 1.)

Using the foregoing procedure, 20 other kinds of catalysts having various compositions and surface areas were prepared.

As the rubidium and cesium sources in the examples, rubidium nitrate and cesium nitrate were employed in all cases. As the sodium source, sodium nitrate was employed in all cases.

The catalysts were used in the ammoxidation of tert-butanol and isobutylene as described below.

(2) Ammoxidation Reaction (A) of Tert-Butanol

Various catalysts prepared in (1) above, were each charged in an amount of 1300 g into a 3-inch diameter fluidized bed reactor equipped internally with a 16-mesh stainless steel gauze, the reaction temperature was maintained at 420°–430° C. and the gage reaction pressure at 0.2 kg/$cm^2$;

the volume ratio of tert-butanol to ammonia was maintained at 1:1.45;

the volume ratio of tert-butanol to air was controlled so that the oxygen concentration in the gas mixture at the catalyst bed outlet was 0.3 volume % or less, except for Comparative Examples 1–3;

a gaseous mixture of tert-butanol, ammonia and air was passed through the reactor at the rate of 550 liters/hr (as calculated at normal conditions of temperature (0° C.) and pressure (1 atm));

the volume ratio of tert-butanol to the air in the mixture was 1:12.5–14 in Comparative Examples 1–3, while other examples were carried out at ratios of 1:10–10.7.; and the contact time under the foregoing reaction conditions was 4.6 seconds.

The results of these ammoxidation reactions are presented in Table 1 together with the compositions of the catalysts employed.

(3) Ammoxidation Reaction (B) of Tert-Butanol

A quantity (1 g) of each catalyst prepared in (1), above, was charged to a glass reaction tube (i.e., a fixed catalyst bed reactor) having an inner diameter of 8 mm, which was maintained at 420° to 430° C., and a gaseous mixture of tert-butanol, ammonia and oxygen diluted with helium to a tert-butanol concentration of 6 volume % was passed therethrough at a rate so as to give a contact time of 1.5 to 3.0 seconds. The reaction was carried out at atmospheric pressure.

The volume ratio of tert-butanol to ammonia was 1:1.5 and the volume ratio of tert-butanol to oxygen was controlled at 1:1.9–2.3 so as to maintain the concentration of oxygen in the gaseous mixture at the catalyst bed outlet (as determined by gas chromatography) at below 0.5 volume %, except for Comparative Examples 9 and 10, where the volume ratio of tert-butanol to oxygen was 1:3.

The results of these ammoxidation reactions are presented in Table 2 together with the catalyst compositions.

In Tables 1, 2 and 3, the total conversion of tert-butanol, the conversion of isobutylene, the yield of methacrylonitrile, and the yield of methacrolein were determined in each example according to the following formulas:

Total conversion of tert-butanol (%) =

$$\left(1 - \frac{\text{Carbon weight of remaining isobutylene}}{\text{Carbon weight of tert-butanol supplied}}\right) \times 100$$

Conversion of isobutylene (%) =

$$\left(1 - \frac{\text{Carbon weight of remaining isobutylene}}{\text{Carbon weight of isobutylene supplied}}\right) \times 100$$

Yield of methacrylonitrile (%) =

$$\frac{\text{Carbon weight of methacrylonitrile formed}}{\text{Carbon weight of tert-butanol and/or isobutylene supplied}} \times 100$$

Yield of methacrolein (%) =

$$\frac{\text{Carbon weight of methacrolein formed}}{\text{Carbon weight of tert-butanol and/or isobutylene supplied}} \times 100$$

In all the examples, no unreacted tert-butanol was detected.

(4) Ammoxidation of Isobutylene

A quantity (1 g) of each catalyst prepared in (1) was charged to a glass reaction tube (i.e., a fixed catalyst bed reactor) having an inner diameter of 8 mm, which was maintained at 420° C. to 430° C., and a gaseous mixture of isobutylene, ammonia and oxygen diluted with helium to an isobutylene concentration of 6 volume % was passed therethrough at a rate so as to give a contact time of 1.5 to 3.0 seconds. The reaction was carried out at atmospheric pressure.

The volume ratio of isobutylene to ammonia was 1:1.5 and the volume ratio of isobutylene to oxygen was controlled at 1:1.9-2.3 so as to maintain the volume of oxygen in the gaseous mixture at the catalyst bed outlet (as determined by gas chromatography) at 0.5 volume %, except for Comparative Examples 17, 18 and 19, wherein the volume ratio of isobutylene to oxygen was 1:3.

The results of the ammoxidation reactions of isobutylene are presented in Table 3 together with the catalyst compositions.

In Table 1, Examples 1-5 illustrate the high methacrylonitrile yields obtained according to the present invention. In Comparative Examples 1-3, the oxygen concentrations in the gaseous mixture at the catalyst bed outlet are too high; in Comparative Examples 4-6 the catalyst surface areas are too large; and in Comparative Example 7, the catalyst is deficient in component A. Thus, all of the Comparative Examples 1-8 are outside the ranges of the present invention, and consequently give lower methacrylonitrile yields. Moreover, in Comparative Examples 4, 5, 6 and 7, carbon deposition occurred on the catalyst.

In Table 2, Examples 6-14 further illustrate the high methacrylonitrile yields obtained according to the present invention. In Comparative Examples 9 and 10, the oxygen concentrations in the gaseous mixture at the catalyst bed outlet are too high; in Comparative Examples 11-13 the atomic ratios of bismuth or iron to molybdenum are outside the scope of the invention; and Comparative Example 14 contains too much of component A. Thus, all of the Comparative Examples 9-14 are outside the ranges of the present invention, and consequently give lower methacrylonitrile yields. Moreover, in Comparative Example 11, carbon deposition occured on the catalyst. When carbon deposition occurred, the yield of methacrolein always increased. The amount of carbon deposition measured on the catalyst was 0.3 to 1.0 gram per 100 grams of catalyst. On the other hand, the amount of carbon deposited on the catalyst according to the examples of the invention was at most 0.05 gram per 100 grams of catalyst.

When using the same catalyst, the yields of methacrylonitrile reported in Table 1 are lower than those of Table 2. This is a phenomenon generally observed as the difference between the fluidized bed reaction and the fixed bed reaction.

In Table 3, Examples 15-17 further illustrate the high methacrylonitrile yields obtained according to the present invention. On the other hand, Comparative Example 15 is too high in oxygen concentration in the gaseous mixture at the catalyst bed outlet; Comparative Example 16 is too high in catalyst surface area; and Comparative Example 17 is too low in catalyst surface area; Comparative Example 18 is deficient in component A, and Comparative Example 19 is deficient with respect to the atomic ratio of iron to molybdenum. Thus, all of the Comparative Examples 15-19 are outside the ranges of the present invention and consequently give low methacrylonitrile yields. Moreover, in Comparative Examples 16 and 18, carbon deposits were formed on the catalysts.

In the ammoxidation reaction (A) of tert-butanol, the ammoxidation reaction (B) of tert-butanol, and the ammoxidation reaction of isobutylene, all the reported values were measured 24 to 100 hours after the reactions began. However, in instances where methacrolein formation abruptly increased and carbon deposition on the catalyst was noticed, the reactions were discontinued prior to said reaction time.

TABLE 1

Ammoxidation reaction tests of tert-butanol

| | Cat. No. | Catalyst composition | Carrier | Cat. Calcination temp. (°C.) | Cat. Calcination time (hrs) | BET surface area (m²/g) |
|---|---|---|---|---|---|---|
| Examples | | | | | | |
| 1 | 1 | $Mo_{12}Bi_{4.6}Fe_{4.9}K_{0.3}P_{1.0}$ | $SiO_2$ 50 wt % | 690 | 4 | 3.0 |
| 2 | 2 | " | $SiO_2$ 50 wt % | 690 | 2 | 4.0 |
| 3 | 3 | $Mo_{12}Bi_{5.3}Fe_{7.2}K_{0.3}P_{2.0}$ | $SiO_2$ 50 wt % | 700 | 2 | 3.5 |
| 4 | 4 | $Mo_{12}Bi_{4.5}Fe_{4.5}Na_{1.2}K_{0.24}P_{1.0}$ | $SiO_2$ 50 wt % | 680 | 5 | 5.0 |
| 5 | 5 | $Mo_{12}Bi_{3.0}Fe_{5.6}K_{0.20}P_{0.6}$ | $SiO_2$ 40 wt % | 690 | 2 | 3.2 |
| Comparative | | | | | | |

TABLE 1-continued

Ammoxidation reaction tests of tert-butanol

| Examples | Cat. No. | Catalyst composition | Carrier | Cat. Calcination temp. (°C.) | Cat. Calcination time (hrs) | BET surface area (m²/g) |
|---|---|---|---|---|---|---|
| 1 | 1 | $Mo_{12}Bi_{4.6}Fe_{4.9}K_{0.3}P_{1.0}$ | $SiO_2$ 50 wt % | 690 | 4 | 3.0 |
| 2 | 2 | " | $SiO_2$ 50 wt % | 690 | 2 | 4.0 |
| 3 | 4 | $Mo_{12}Bi_{4.5}Fe_{4.5}Na_{1.2}K_{0.24}P_{1.0}$ | $SiO_2$ 50 wt % | 680 | 5 | 5.0 |
| 4 | 6 | $Mo_{12}Bi_{4.6}Fe_{4.9}K_{0.3}P_{1.0}$ | $SiO_2$ 50 wt % | 630 | 2 | 13.5 |
| 5 | 7 | $Mo_{12}Bi_{5.3}Fe_{7.2}K_{0.1}P_{2.0}$ | $SiO_2$ 50 wt % | 660 | 1 | 18.5 |
| 6 | 8 | " | $SiO_2$ 60 wt % | 600 | 1 | 39.0 |
| 7 | 9 | $Mo_{12}Bi_{4.6}Fe_{4.9}K_{0.02}P_{1.0}$ | $SiO_2$ 50 wt % | 700 | 4 | 3.8 |
| 8 | 10 | $Mo_{12}Bi_{8.8}Fe_{13}K_{0.1}P_{1.2}$ | $SiO_2$ 50 wt % | 690 | 5 | 6.5 |

|  | Cat. No. | Reaction temp. (°C.) | Oxygen conc. in gas mix. at cat. bed outlet | Total conversion of t-butanol (vol %) | Yield of methacrylonitrile (%) | Yield of methacrolein (%) |
|---|---|---|---|---|---|---|
| Examples |  |  |  |  |  |  |
| 1 | 1 | 430 | 0.20 | 99.6 | 78.3 | 1.5 |
| 2 | 2 | 430 | 0.15 | 99.7 | 77.9 | 1.3 |
| 3 | 3 | 430 | 0.08 | 99.5 | 75.1 | 1.6 |
| 4 | 4 | 420 | 0.10 | 99.2 | 75.5 | 1.0 |
| 5 | 5 | 430 | 0.08 | 99.7 | 74.8 | 1.5 |
| Comparative Examples |  |  |  |  |  |  |
| 1 | 1 | 430 | 1.30 | 92.5 | 61.2 | 2.6 |
| 2 | 2 | 430 | 1.40 | 94.8 | 60.1 | 2.9 |
| 3 | 4 | 420 | 1.25 | 93.0 | 58.8 | 2.3 |
| 4 | 6 | 430 | 0.10 | 96.3 | 67.5 | 5.0 |
| 5 | 7 | 430 | 0.13 | 94.2 | 60.2 | 7.3 |
| 6 | 8 | 420 | 0.15 | 93.7 | 57.2 | 8.5 |
| 7 | 9 | 430 | 0.07 | 93.1 | 53.0 | 6.5 |
| 8 | 10 | 430 | 0.13 | 96.6 | 50.5 | 3.0 |

TABLE 2

Ammoxidation reaction tests of tert-butanol

|  | Cat. No. | Catalyst composition | Carrier | Cat. Calcination temp. (°C.) | Cat. Calcination time (hrs) | BET surface area (m²/g) |
|---|---|---|---|---|---|---|
| Examples |  |  |  |  |  |  |
| 6 | 1 | $Mo_{12}Bi_{4.6}Fe_{4.9}K_{0.3}P_{1.0}$ | $SiO_2$ 50 wt % | 690 | 4 | 3.0 |
| 7 | 4 | $Mo_{12}Bi_{4.5}Fe_{4.5}Na_{1.2}K_{0.24}P_{1.0}$ | $SiO_2$ 50 wt % | 680 | 5 | 5.0 |
| 8 | 5 | $Mo_{12}Bi_{3.0}Fe_{5.6}K_{0.20}P_{0.6}$ | $SiO_2$ 40 wt % | 690 | 2 | 3.2 |
| 9 | 11 | $Mo_{12}Bi_{4.5}Fe_{4.2}Rb_{0.15}P_{1.2}$ | $SiO_2$ 50 wt % | 700 | 3 | 4.5 |
| 10 | 12 | $Mo_{12}Bi_{4.5}Fe_{4.2}K_{0.2}Cs_{0.1}P_{1.2}$ | $SiO_2$ 50 wt % | 700 | 3 | 4.3 |
| 11 | 13 | $Mo_{12}Bi_{8.4}Fe_{6.6}K_{0.3}P_{2.0}$ | $SiO_2$ 40 wt % | 700 | 4 | 5.0 |
| 12 | 14 | $Mo_{12}Bi_{11}Fe_4K_{0.2}P_1$ | $SiO_2$ 50 wt % | 690 | 4 | 6.2 |
| 13 | 15 | $Mo_{12}Bi_{5.75}Fe_9K_{0.3}P_1$ | $SiO_2$ 50 wt % | 690 | 4 | 5.3 |
| 14 | 16 | $Mo_{12}Bi_{2.5}Fe_{3.9}K_{0.3}P_{0.5}$ | $SiO_2$ 50 wt % | 690 | 4 | 2.5 |
| Comparative Examples |  |  |  |  |  |  |
| 9 | 1 | $Mo_{12}Bi_{4.6}Fe_{4.9}K_{0.3}P_{1.0}$ | $SiO_2$ 50 wt % | 690 | 4 | 3.0 |
| 10 | 4 | $Mo_{12}Bi_{4.5}Fe_{4.5}Na_{1.2}K_{0.24}P_{1.0}$ | $SiO_2$ 50 wt % | 680 | 5 | 5.0 |
| 11 | 17 | $Mo_{12}Bi_{13.7}Fe_{12.5}K_{0.1}P_{1.0}$ | $SiO_2$ 50 wt % | 690 | 4 | 3.5 |
| 12 | 18 | $Mo_{12}Bi_{0.8}Fe_{4.5}K_{0.2}P_{1.0}$ | $SiO_2$ 50 wt % | 700 | 2 | 2.8 |
| 13 | 19 | $Mo_{12}Bi_{4.5}Fe_{1.0}K_{0.2}P_{1.0}$ | $SiO_2$ 50 wt % | 700 | 2 | 2.7 |
| 14 | 20 | $Mo_{12}Bi_{4.6}Fe_{4.9}K_{1.5}P_{1.0}$ | $SiO_2$ 50 wt % | 690 | 2 | 2.8 |

Oxygen conc.                                                       Yield of

TABLE 2-continued

Ammoxidation reaction tests of tert-butanol

| | Cat. No. | Reaction temp. (°C.) | in gas mix. at cat. bed outlet | Total conversion of t-butanol (vol %) | methacrylonitrile (%) | Yield of methacrolein (%) |
|---|---|---|---|---|---|---|
| Examples | | | | | | |
| 6 | 1 | 430 | 0.30 | 99.3 | 82.1 | 1.7 |
| 7 | 4 | 420 | 0.15 | 99.4 | 80.3 | 1.2 |
| 8 | 5 | 430 | 0.15 | 99.3 | 80.0 | 1.5 |
| 9 | 11 | 430 | 0.23 | 99.5 | 78.3 | 1.8 |
| 10 | 12 | 430 | 0.40 | 99.2 | 79.1 | 1.9 |
| 11 | 13 | 430 | 0.18 | 99.8 | 78.8 | 1.4 |
| 12 | 14 | 430 | 0.30 | 99.7 | 75.7 | 1.8 |
| 13 | 15 | 430 | 0.15 | 99.8 | 77.3 | 2.0 |
| 14 | 16 | 430 | 0.20 | 98.8 | 78.9 | 2.1 |
| Comparative Examples | | | | | | |
| 9 | 1 | 430 | 2.0 | 93.8 | 62.5 | 2.9 |
| 10 | 4 | 420 | 1.65 | 94.3 | 60.8 | 3.0 |
| 11 | 17 | 430 | 0.10 | 98.5 | 58.5 | 8.3 |
| 12 | 18 | 430 | 0.15 | 95.8 | 57.0 | 3.1 |
| 13 | 19 | 430 | 0.20 | 94.0 | 62.1 | 3.5 |
| 14 | 20 | 420 | 0.33 | 90.2 | 58.5 | 5.8 |

TABLE 3

Ammoxidation reaction tests of isobutylene

| | Cat. No. | Catalyst composition | Carrier | Cat. Calcination temp. (°C.) | Cat. Calcination time (hrs) | BET surface area (m$_2$/g) |
|---|---|---|---|---|---|---|
| Examples | | | | | | |
| 15 | 1 | $Mo_{12}Bi_{4.6}Fe_{4.9}K_{0.3}P_{1.0}$ | $SiO_2$ 50 wt % | 690 | 4 | 3.0 |
| 16 | 4 | $Mo_{12}Bi_{4.5}Fe_{4.5}Na_{1.2}K_{0.24}P_{1.0}$ | $SiO_2$ 50 wt % | 680 | 5 | 5.0 |
| 17 | 5 | $Mo_{12}Bi_{3.0}Fe_{5.6}K_{0.20}P_{0.6}$ | $SiO_2$ 40 wt % | 690 | 2 | 3.2 |
| Comparative Examples | | | | | | |
| 15 | 1 | $Mo_{12}Bi_{4.6}Fe_{4.9}K_{0.3}P_{1.0}$ | $SiO_2$ 50 wt % | 690 | 4 | 3.0 |
| 16 | 7 | $Mo_{12}Bi_{5.3}Fe_{7.2}K_{0.1}P_{2.0}$ | $SiO_2$ 50 wt % | 660 | 1 | 18.5 |
| 17 | 21 | $Mo_{12}Bi_{4.6}Fe_{4.9}K_{0.3}P_{1.0}$ | $SiO_2$ 50 wt % | 730 | 6 | 1.8 |
| 18 | 9 | $Mo_{12}Bi_{4.6}Fe_{4.9}K_{0.02}P_{1.0}$ | $SiO_2$ 50 wt % | 700 | 4 | 3.8 |
| 19 | 19 | $Mo_{12}Bi_{4.5}Fe_{1.0}K_{0.2}P_{1.0}$ | $SiO_2$ 50 wt % | 700 | 2 | 2.8 |

| | Cat. No. | Reaction temp. (°C.) | Oxygen conc. in gas mix. at cat. bed outlet | Total conversion of i-butylene (vol. %) | Yield of methacrylonitrile (%) | Yield of methacrolein (%) |
|---|---|---|---|---|---|---|
| Examples | | | | | | |
| 15 | 1 | 430 | 0.22 | 99.4 | 82.0 | 1.4 |
| 16 | 4 | 420 | 0.12 | 99.3 | 80.1 | 1.3 |
| 17 | 5 | 430 | 0.18 | 99.2 | 80.0 | 1.5 |
| Comparative Examples | | | | | | |
| 15 | 1 | 430 | 1.85 | 94.0 | 63.0 | 3.3 |
| 16 | 7 | 430 | 0.20 | 96.4 | 64.5 | 8.9 |
| 17 | 21 | 430 | 0.48 | 90.5 | 59.7 | 5.3 |
| 18 | 9 | 430 | 0.07 | 95.3 | 58.3 | 7.6 |
| 19 | 19 | 430 | 0.18 | 93.6 | 60.0 | 3.4 |

(5) Life Test of the Catalyst

Using Catalyst No. 1 and the apparatus described in connection with the ammoxidation reaction (A) of tert-butanol, a continuous run was carried out under the conditions of Example 1.

The oxygen concentration in the gas mixture at the catalyst bed outlet was maintained during the operation at or below 0.3 volume %.

During a continuous run of 1000 hours, the total conversion of tert-butanol was 99% or more, the methacrylonitrile yield was approximately constant at 77.8–78.3%, and no observable carbon deposits were formed on the catalyst.

When continuous ammoxidation of tert-butanol was performed for 50 hours using Catalyst No. 1 under the conditions of Example 1, except for maintaining the oxygen concentration in the gaseous mixture at the catalyst bed outlet at 1.3 to 1.5 volume %, the rate of formation of by-product methacrolein increased with time and a tendency toward carbon deposition on the catalyst was observed.

On the the other hand, when a continuous run was performed under the conditions of Example 1 using Catalyst No. 6 and the apparatus described in connection with the ammoxidation reaction (A) of tert-butanol, methacrolein by-product is markedly increased after 50 hours, and carbon was deposited on the catalyst at the rate of 0.5 g/100 g of catalyst, whereby the catalyst was blackened and the yield of methacrylonitrile markedly decreased.

These results are summarized in Table 4.

TABLE 4

Effect of prolonged run on ammoxidation

| Catalyst No. | Chemical composition/carrier | Surface area (m²/g) | O₂ in gaseous reaction product Mixture (vol. %) | Running time (hours) | Results Conversion (%) | Yield (%) MAN | Yield (%) methacrolein |
|---|---|---|---|---|---|---|---|
| 1 | Mo$_{12}$Bi$_{4.6}$Fe$_{4.9}$K$_{0.3}$P$_{1.0}$/SiO$_2$ (50 wt. %) | 3 | ca. 0.3 | 5 | 99.3 | 77.8 | 2.0 |
|   |   |   | " | 24 | 99.5 | 78.0 | 1.5 |
|   |   |   | " | 50 | 99.6 | 78.3 | 1.5 |
|   |   |   | " | 100 | 99.7 | 78.0 | 1.6 |
|   |   |   | " | 1,000 | 99.3 | 78.0 | 2.0$^{(3)}$ |
| 6 | Mo$_{12}$Bi$_{4.6}$Fe$_{4.9}$K$_{0.3}$P$_{1.0}$/SiO$_2$ (50 wt. %) | 13.5 | ca. 0.3 | 5 | 99.5 | 70.5 | 3.0 |
|   |   |   | " | 24 | 96.3 | 67.5 | 5.0$^{(1)}$ |
|   |   |   | " | 50 | 90.3 | 62.0 | 7.3$^{(2)}$ |
| 1 | Mo$_{12}$Bi$_{4.6}$Fe$_{4.9}$K$_{0.3}$P$_{1.0}$/SiO$_2$ (50 wt. %) | 3 | 1.3–1.5 | 5 | 93.5 | 61.1 | 2.8 |
|   |   |   | " | 24 | 92.5 | 61.2 | 2.6 |
|   |   |   | " | 50 | 92.4 | 60.9 | 3.0 |

$^{(1)}$Methacrolein formation increases after 24 hours
$^{(2)}$Catalyst blackend by carbon deposition (0.5 g/100 g catalyst)
$^{(3)}$No carbon deposition on catalyst was observed.

The foregoing examples illustrate, without limitation, the catalyst and process of the present invention. It is understood that changes and variations can be in the examples without departing from the spirit and scope of the invention as defined in the following claims.

Having thus described our invention, what we claim as new and desire to secure by Letters Patent is:

1. A process for preparing methacrylonitrile by reacting isobutylene or tertiary butanol with ammonia and oxygen in a gaseous phase, comprising:
(A) carrying out the reaction
  (i) on a catalyst system consisting essentially of (1) 30–70% by weight of a silica catalyst carrier and (2) a catalyst having a composition represented by the following general formula:

$$A_aMo_{12}Bi_bFe_cNa_dP_eO_x$$

wherein
A is at least one element selected from the group consisting of potassium, rubidium and cesium, and a, b, c, d, e and x are the atomic ratios of A, bismuth, iron, sodium, phosphorus and oxygen, respectively, relative to twelve atoms of molybdenum, wherein:
a is between 0.05 and 1.0
b is between 1 and 18,
c is between 2 and 10,
d is between 0 and 3.6,
e is between 0 and 3, and
x is the number of oxygen atoms required to satisfy the valence requirements of the other elements present, said catalyst having a surface area of 2.5–6.2 m²/g, and a feedstock conversion rate with no substantial decrease in conversion percentage points from the initial value while producing carbon deposition of less than 0.05 g carbon/100 g catalyst, after 1000 hours of continuous use;
  (ii) at a reaction temperature of 380° C. to 480° C.; and
  (iii) at a contact time of 1 to 10 seconds; and
(B) maintaining the oxygen volume concentration in the gaseous reaction mixture at the outlet of the catalyst bed below about one percent.

2. Process of claim 1 wherein:
b is between 2 and 10;
c is between 3 and 10;
the silica constitutes between 40 and 60% by weight of the total catalyst system;
the catalyst system demonstrates a time conversion of feedstock with no substantial decrease in conversion percentage points from the initial value;
the reaction temperature is between about 400° C. and about 460° C.;
the contact time is between about 1.5 seconds and about 8 seconds; and
the oxygen volume concentration in the gaseous reaction mixture at the outlet of the catalyst bed is maintained below about 0.5%.

3. Process of claim 2 wherein A is potassium and a is between 0.1 and 1.0.

4. Process of claim 2 wherein A is rubidium or cesium and a is between 0.05 and 0.6.

5. Process of claim 3 or 4 wherein a is between 0.1 and 0.6.

6. Process of claim 1 wherein:
the volume ratio of tert-butanol and/or isobutylene to ammonia in the gaseous phase is between about 1:0.9 and about 1:2.0; and
the volume ratio of tert-butanol and/or isobutylene to oxygen in the gaseous phase is between about 1:1.8 and about 1:2.6.

7. Process of claim 6 wherein the volume ratio of tert-butanol and/or isobutylene to ammonia in the gaseous phase is between about 1:1 and about 1:1.6.

* * * * *